US00PP25256P2

(12) United States Plant Patent
Wain

(10) Patent No.: US PP25,256 P2
(45) Date of Patent: Jan. 27, 2015

(54) ***CHRYSANTHEMUM* PLANT NAMED 'FIMMERDABRO'**

(50) Latin Name: *Chrysanthemum×morifolium*
Varietal Denomination: Fimmerdabro

(71) Applicant: Peter Wain, Locks Heath (GB)

(72) Inventor: Peter Wain, Locks Heath (GB)

(73) Assignee: Fides B.V., De Lier (NL)

( * ) Notice: Subject to any disclaimer, the term of this patent is extended or adjusted under 35 U.S.C. 154(b) by 130 days.

(21) Appl. No.: 13/815,200

(22) Filed: Feb. 8, 2013

(51) Int. Cl.
*A01H 5/00* (2006.01)

(52) U.S. Cl.
USPC ..... Plt./296

(58) Field of Classification Search
USPC ..... Plt./296
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Fimmerdabro', characterized by its upright to outwardly spreading and uniformly mounded plant habit; freely branching habit; dense and full plant habit; uniform and freely flowering habit; medium to large decorative-type inflorescences with dark bronze-colored ray florets; early September flowering response under natural season conditions; and good garden performance.

1 Drawing Sheet

Botanical designation: *Chrysanthemum×morifolium.*
Cultivar denomination: 'FIMMERDABRO'.

BACKGROUND OF THE INVENTION

The present invention relates to a new and distinct *Chrysanthemum* plant, botanically known as *Chrysanthemum×morifolium*, commercially grown as a garden *Chrysanthemum* and hereinafter referred to by the name 'Fimmerdabro'.

The new *Chrysanthemum* plant is a product of a planned breeding program conducted by the Inventor in Fareham, Hampshire, United Kingdom. The objective of the breeding program is to create new early-flowering garden *Chrysanthemum* plants with numerous attractive inflorescences.

The new *Chrysanthemum* plant originated from a cross-pollination made in January, 2007 by the Inventor in Fareham, Hampshire, United Kingdom of a proprietary selection of *Chrysanthemum×morifolium* identified as code number 82606, not patented, as the female, or seed, parent with a proprietary selection of *Chrysanthemum×morifolium* identified as code number G003, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2007.

Asexual reproduction of the new *Chrysanthemum* by terminal vegetative cuttings was first conducted in Fareham, Hampshire, United Kingdom in December, 2007. Asexual reproduction by terminal vegetative cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmerdabro'. These characteristics in combination distinguish 'Fimmerdabro' as a new and distinct *Chrysanthemum* plant:

1. Upright to outwardly spreading and uniformly mounded plant habit.
2. Freely branching habit; dense and full plant habit.
3. Uniform and freely flowering habit.
4. Medium to large decorative-type inflorescences with dark bronze-colored ray florets.
5. Plants flower under natural season conditions the first week of September in the United Kingdom.
6. Good garden performance.

Plants of the new *Chrysanthemum* can be compared to plants of the female parent selection. Plants of the new *Chrysanthemum* differ from plants of the female parent selection, in the following characteristics:

1. Plants of the new *Chrysanthemum* have slightly smaller inflorescences than plants of the female parent selection.
2. Plants of the new *Chrysanthemum* and the female parent selection differ in ray floret color as plants of the female parent selection have apricot-colored ray florets.

Plants of the new *Chrysanthemum* can be compared to plants of the male parent selection. Plants of the new *Chrysanthemum* differ from plants of the male parent selection, in the following characteristics:

1. Plants of the new *Chrysanthemum* flower earlier than plants of the male parent selection under natural season conditions.
2. Plants of the new *Chrysanthemum* and the male parent selection differ in ray floret color as plants of the male parent selection have red-colored ray florets.

Plants of the new *Chrysanthemum* can be compared to plants of *Chrysanthemum×morifolium* 'Yotabitha', disclosed in U.S. Plant Pat. No. 16,110. In side-by-side comparisons conducted in Fareham, Hampshire, United Kingdom, plants of the new *Chrysanthemum* differed from plants of 'Yotabitha' in the following characteristics:

1. Plants of the new *Chrysanthemum* flowered later than plants of 'Yotabitha' under natural season conditions.
2. Plants of the new *Chrysanthemum* and 'Yotabitha' differed in ray floret color as plants of 'Yotabitha' had red-colored ray florets.

BRIEF DESCRIPTION OF THE PHOTOGRAPH

The accompanying photograph illustrates the overall appearance of the new *Chrysanthemum* showing the colors as true as it is reasonably possible to obtain in colored reproductions of this type. Colors in the photograph may differ slightly from the color values cited in the detailed botanical description which accurately describe the colors of the new *Chrysanthemum.*

The photograph comprises a top perspective view of a typical flowering plant of 'Fimmerdabro' grown in a container.

DETAILED BOTANICAL DESCRIPTION

The aforementioned photograph and following observations and measurements describe plants grown during the late summer and early autumn in 19-cm containers in an outdoor nursery in Fareham, Hampshire, United Kingdom and under cultural practices typical of commercial garden *Chrysanthemum* production. During the production of the plants, day temperatures ranged from 10° C. to 25° C., night temperatures ranged from 5° C. to 15° C. and light levels ranged from 400 to 2,500 joules. Plants were pinched one time and were about 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fimmerdabro'.

Parentage:

*Female, or seed, parent.*—Proprietary selection of *Chrysanthemum×morifolium* identified as code number 82606, not patented.

*Male, or pollen, parent.*—Proprietary selection of *Chrysanthemum×morifolium* identified as code number G003, not patented.

Propagation:

*Type.*—Terminal vegetative cuttings.

*Time to initiate roots, summer.*—About ten days at temperatures of about 21° C.

*Time to initiate roots, winter.*—About twelve days at temperatures of about 21° C.

*Time to produce a rooted young plant, summer.*—About three weeks at temperatures of about 21° C.

*Time to produce a rooted young plant, winter.*—About four weeks at temperatures of about 21° C.

*Root description.*—Fine, fibrous; light brown in color.

*Rooting habit.*—Freely branching; dense.

Plant description:

*Plant and growth habit.*—Herbaceous decorative-type garden *Chrysanthemum*; stems upright to outwardly spreading giving a uniformly mounded appearance to the plant; numerous lateral branches and relatively short internodes, dense and full plant habit; moderately vigorous growth habit.

*Plant height.*—About 24 cm.

*Plant width.*—About 38 cm.

*Branching habit.*—Freely branching habit, about eight lateral branches develop after removal of terminal apex (pinching); each primary lateral with numerous secondary laterals.

*Lateral branches.*—Length: About 20 cm. Diameter: About 6 mm. Internode length: About 3 mm. Strength: Strong, brittle. Aspect: About 80° from stem. Texture: Fine pubescence. Color: Close to 146D.

*Leaves.*—Arrangement: Alternate, simple. Length: About 4.5 cm. Width: About 2.9 cm. Shape: Palmately-lobed; roughly ovate. Apex: Acuminate and mucronate. Base: Obtuse with truncate tendencies. Margin: Palmately lobed, sinuses between lateral lobes parallel to divergent; slightly dentate. Texture, upper and lower surfaces: Fine pubescence; veins prominent on lower surface. Color: Developing leaves, upper surface: Close to N137B. Developing leaves, lower surface: Close to N138B. Fully expanded leaves, upper surface: Close to 137B; venation, close to 138C. Fully expanded leaves, lower surface: Close to 138B; venation, close to 138C. Petiole: Length: About 1 cm. Diameter: About 3 mm. Texture, upper and lower surfaces: Fine pubescence. Color, upper and lower surfaces: Close to 138C.

Inflorescence description:

*Form and flowering habit.*—Decorative-type inflorescence form with oblanceolate-shaped ray florets; inflorescences borne on terminals above and beyond the foliar plane; disc and ray florets arranged acropetally on a capitulum; freely flowering habit with about 13 inflorescences developing per lateral branch and about 390 inflorescences developing per plant.

*Fragrance.*—Fragrant; pungent, herbaceous.

*Flowering response.*—Early flowering habit, plants exposed to natural season conditions begin flowering the first week of September in the United Kingdom; with photoinductive treatments, response time is about 35 days.

*Inflorescence longevity.*—Inflorescences maintain good color and substance for about three to five weeks on the plant; inflorescences persistent.

*Inflorescence buds.*—Height: About 8 mm. Diameter: About 8 mm. Shape: Oblate. Color: Close to 138C.

*Inflorescence height.*—About 1.3 cm.

*Inflorescence diameter.*—About 4.8 cm.

*Receptacles.*—Height: About 4 mm. Diameter: About 3 mm. Shape: Ovoid. Color: Close to 145C.

*Ray florets.*—Orientation: Initially upright, then about 80° to 90° from vertical. Length: About 2.1 cm. Width: About 7 mm. Shape: Oblanceolate. Apex: Emarginate. Base: Fused into a short tube. Margin: Entire. Texture, upper and lower surfaces: Smooth, glabrous. Number of ray florets per inflorescence: About 125 arranged in about eleven whorls. Color: When opening, upper surface: Close to 44A. When opening, lower surface: Close to 25D. Fully opened, upper surface: Close to 44B; color becoming closer to 44D with development. Fully opened, lower surface: Close to 32D; color does not change with development.

*Disc florets.*—Disc floret development has not been observed on plants of the new *Chrysanthemum.*

*Phyllaries*.—Number of phyllaries per inflorescence: About 25 arranged in about four whorls. Length: About 6 mm. Width: About 2 mm. Shape: Obovate. Apex: Acute to obtuse. Base: Truncate, fused. Margin: Entire. Texture, upper surface: Smooth, glabrous. Texture, lower surface: Fine pubescence. Color, upper surface: Close to 137D. Color, lower surface: Close to 137C.

*Peduncles*.—Length, terminal peduncle: About 6.5 cm. Diameter, terminal peduncle: About 3 mm. Angle: Erect to about 30° from vertical. Strength: Moderately strong; flexible. Texture: Fine pubescence. Color: Close to 146D.

*Reproductive organs*.—Androecium: None observed. Gynoecium: Pistil length: About 1 cm. Stigma shape: Bi-parted. Stigma color: Close to 12A. Style length: About 4 mm. Style color: Close to 1D. Ovary color: Close to 157D.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum* grown under commercial conditions.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmerdabro' as illustrated and described.

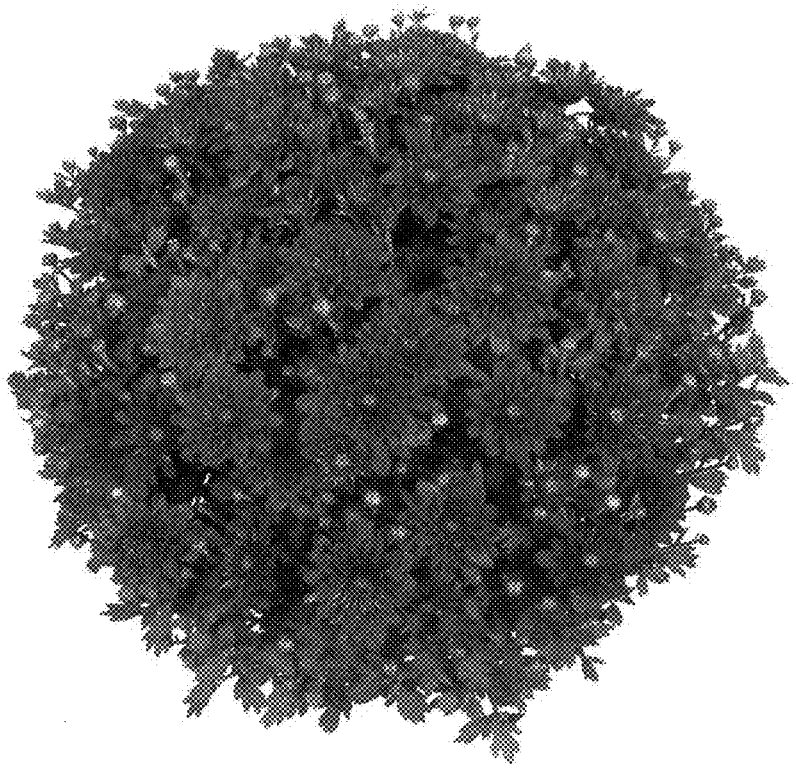

* * * * *